United States Patent [19]

Renoux et al.

[11] 4,148,885

[45] Apr. 10, 1979

[54] IMMUNOSTIMULANT MEDICINE

[75] Inventors: Gerard E. Renoux; Micheline Renoux, both of Tours, France

[73] Assignee: Institut Merieux, France

[21] Appl. No.: 687,505

[22] Filed: May 18, 1976

Related U.S. Application Data

[63] Continuation-in-part of Ser. No. 509,318, Sep. 25, 1974, abandoned.

[30] Foreign Application Priority Data

Sep. 25, 1973 [FR] France .............................. 73 34328

[51] Int. Cl.² ............................................ A61K 33/04
[52] U.S. Cl. ...................................... 424/162; 424/88; 424/164; 424/246; 424/250; 424/253; 424/273 R; 424/275; 424/300; 424/317; 424/323
[58] Field of Search ............... 424/300, 313, 162, 164, 424/273, 275, 246, 250, 323, 88, 317

[56] References Cited

U.S. PATENT DOCUMENTS

| | | | |
|---|---|---|---|
| 2,399,443 | 4/1946 | Masucci | 424/89 |
| 3,429,966 | 2/1969 | Gall | 424/92 |
| 3,452,135 | 6/1969 | Medveczky | 424/9 |
| 3,651,211 | 3/1972 | Gillchriest et al. | 424/89 |

OTHER PUBLICATIONS

Merck Index, 8th ed. 1968 – pp. 674, 812, 967, 968, 1037, 1042, 1043, 1045–1046.
Chemical Abstracts 67: 10156c (1967).
Chemical Abstracts 72: 47352t (1970).

*Primary Examiner*—Leonard Schenkman
*Attorney, Agent, or Firm*—Cushman, Darby & Cushman

[57] ABSTRACT

Immunostimulant medicine comprises one or more sulfur compounds absent as a normal constituent in living beings, said compound comprising between about 16–40 percent sulfur in the molecule thereof, and an excipient therefor.

8 Claims, 1 Drawing Figure

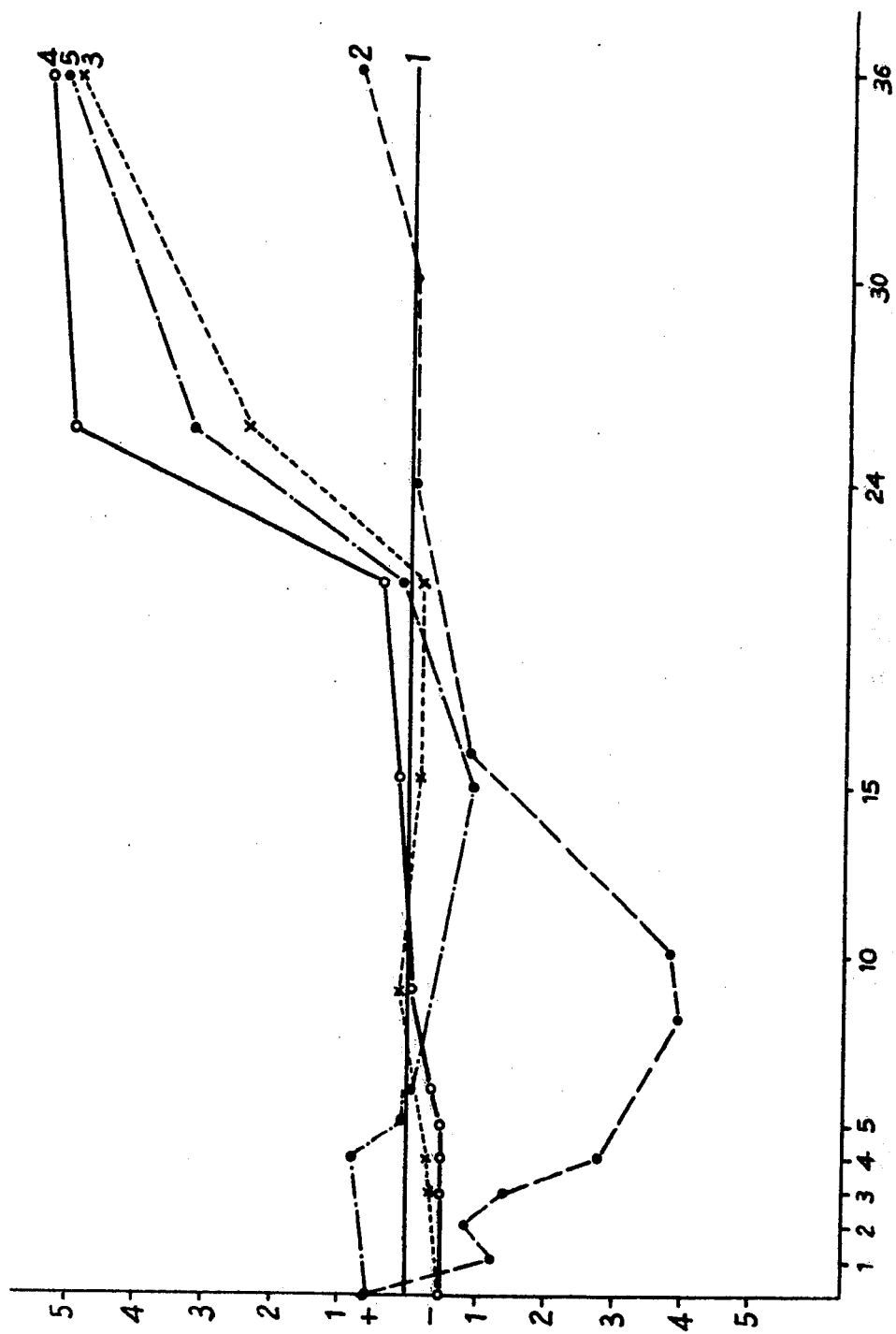

IMMUNOSTIMULANT MEDICINE

The present application is a continuation-in-part application of Ser. No. 509,318 filed Sept. 25, 1974 now abandoned.

The present invention relates to a new medicine for stimulating immunitary responses of a receptor organism.

It is known that the defense mechanism of an organism, briefly categorized as humoral immunity and cellular immunity, interpose to eliminate harmful foreign bodies such as, principally, micro-organisms (bacteria, rickettsies, virus, fungus, protozoans or metazoans) and abnormal cells which comprise neoformed cells which are potentially or effectively capable of becoming a "tumor".

Moreover, a certain number of illnesses are caused, in a well known fashion, by some modification of the functioning of the immunologic system or they accompany such modifications. They are notably the self-immune illnesses, illnesses of immuncomplexes, poisoning, septicemia and the like.

A great number of substances susceptible of increasing the immunologic reactivity of receptor subjects have been tested, this stimulation of the immunity corresponding to a wide range of antigens. For example, the B.C.G. has been utilized in the case of lymphoid or lymphome lucemia; some extracts of M. tuberculosis, of C-parvum and of Brucella, etc.

These substances exhibit, however, several disadvantages. In particular, they are often toxic. They also provoke to various degrees a "producer of local granuloma" effect and, in a general fashion, the lack of knowledge of their exact nature and the difficult conditions of their preparation render complicated a systematic test and good reproducibility of clinical results.

The new medicines according to the present invention overcome these drawbacks and they possess very weak toxicity and in certain cases, none at all. Certain ones at least of the medicines have an antitoxic activity on the organism. They are void of the "producer of local granuloma" effect. The administration of the medicines according to the invention provides a stimulation of specific immunologic response of the organism in the case of introducing an antigen. These medicines act according to the case on the production of antibodies and on cellular immunity and, in a general fashion, on these two aspects of immunity. They permit a re-establishment of normal immunologic reactivity in the patient's body whose immunitary activity has been diminished in a natural or provoked fashion. When the medicine, according to the invention, is combined with a vaccine, it produces an increase in the immunoprotective effect of the vaccine.

The new vaccines according to the invention are susceptible to a sufficiently great number of therapeutic applications. They are principally used either alone, to reestablish a normal immunologic reactivity, or combined with "vaccines" (tumoral cells, cell extracts and oncogene virus). The medicines, according to the invention, are also applicable to the restoration of immunity decreased by age (immunosenescence), caused by a natural deficiency or by a serious modification of the general state.

The new medicines according to the invention can also be used in immunotherapy for burns.

The new immunostimulant medicines are characterized by the fact that they comprise one or more mineral or organic sulfur compounds absent as a normal constituent in living beings, the sulfur comprising about between 16–40% of the molecule. Preferably, the said molecule is a ring compound or is capable of cyclization.

The said molecules possess a low molecular weight and this property can be defined by, for example, representative sulfur compounds described below which constitute or are a part of the medicines according to the present invention.

In a preferred embodiment, a medicine according to the invention properly proportioned for administration to a human being comprises a quantity of sulfur compound, expressed in mg per kg of the receptor organism, sufficient such that the index of stimulation, obtained by dividing the number of plate culture counted for $10^8$ nucleated cells of the mice spleen after stimulation and injection of sheep red blood corpuscles, by the number of plate cultures obtained after injection of sheep red blood corpuscles alone is greater or equal to 1.6. In a general fashion the said dosage is equal preferably to less than 1 mg/kg.

The medicines according to the present invention comprise preferably at least one of the following compounds:

(1) sodium diethyldithiocarbamate

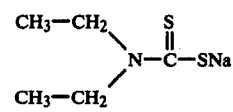

preferably of doses of 10–25 mg/kg (2) sodium thiomalate

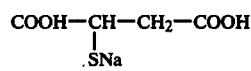

preferably of doses of 0.6–10 mg/kg (3) sodium thiosulfate

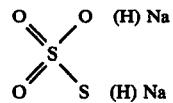

(4) sodium metabisulfite

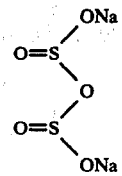

(5) methimazole (1-methyl-2-mercaptoimidazole)

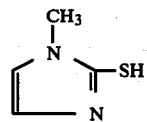

(6) thiophene (7) thioguanine

(8) thiosemicarbazide

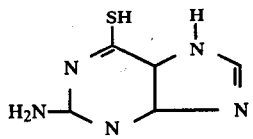

(9) phenothiazine

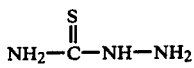

(10) thiouracil

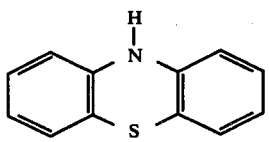

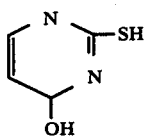

As a variation of the present invention, the said medicines can comprise, in addition to the said sulfur compounds, a certain quantity of theophylline or an aminophylline analogue.

The medicines according to the present invention can advantageously be administered at the same time as a vaccine, principally a vaccine in which the antigens come from tumoral cells, cell extracts or oncogene virus with the view to increase the immunizing power of the vaccine. The addition can be effected simultaneously with the vaccine, or before or after, and preferably, less than 2 days before or after the administration of the vaccine.

The invention is also related to a new immunostimulant medicine comprising a preparation of antigens acting as a vaccine and at least one sulfur compound having from 16–40% sulfur encompassed in the molecule, the said molecule being absent as a normal constituent in living beings.

Such a medicine can advantageously include antigens coming from tumoral cells or their extracts or even viro-oncogenes antigens. Among the said sulfur compounds employed in the said medicine are preferably those compounds specifically identified above.

Such medicines are characterized by a combination effect in which the sulfur compound acting in the manner of an adjuvant potentializes the antigenic action of the vaccine antigens, thus producing an increased immunitary response, even in an organism whose immunologic reactivity has been reduced.

The quantity of the sulfur compound in the dosed medicine is such that the stimulation index is at least equal to 1.6. The dose of sodium diethyldithiocarbamate as well as that of sodium thiomalate is preferably between 1.25 and 25 mg/kg.

The following is a description, as an example, of the action of said medicines on the immunitary response of mice.

The tests permitting the determination of the stimulation index (IS) have been established by counting the plate cultures of hematolysis of mice spleen, localized in gel according to a technique derived from the original method of Jerne. This method in its classic form raises the activity of lymphocytes B (antibody production) to lymphocytes T (cellular immunity and inducing the production of antibodies).

The IS index is obtained by dividing the number of plate cultures counted for $10^8$ nucleated cells of the spleen after an administration of sheep red corpuscles and of the medicine according to the invention, by the number of plate cultures obtained after injection of the red blood corpuscles alone, also for $10^8$ nucleated cells.

By statistical analysis of the results, an IS value $\geq 1.6$ corresponds to effective immunity stimulation whereas an IS value $\leq 0.60$ corresponds to an inhibition.

EXAMPLE 1

One uses groups of 5 laboratory female mice CI-1 (Rivers) weighing 20 ± 1g and one inoculates the said mice intravenously with $10^8$ sheep red blood corpuscles. Certain groups of mice are thus preserved as a control of the antigen activity. The other groups receive simultaneously, but separately, subcutaneously, some different doses per group, of the sulfur compound, the doses ranging from 0.625 mg/kg to 25 mg/kg.

Two days after the injection of antigens and sulfur compound the mice are sacrificed and the spleens examined.

To this effect one mixes in a Petri disk, 100 mm in diameter, 2 ml of an 8% Eagle agar medium containing 3.5 × $10^8$ sheep red blood corpuscles and 0.2 ml of Eagle medium not treated with agar containing in homogeneous suspension and well dispersed one fifth of the mice spleen pulp. After solidification of the medium and incubation for 1 hour at 37° C., one portions out the surface of each dish 1.5 ml of C' diluted to 1/5 in a Mayer veronal buffer and one carries again for 1 hour at 37° C. the fixation on the antigen (sheep red blood corpuscles) of the antibodies diffused around the formative cells and the subsequent cytotoxic effect of C' creating some plate cultures of hematolysis. These plate cultures are registered, counted and their number brought to $10^8$ nucleated spleen cells, at the same time as it is standard deviation calculated.

The results obtained are shown in Table I below.

TABLE 1

STIMULATION INDEX BY SUBCUTANEOUS INJECTION OF THE MEDICINE OF THE PRESENT INVENTION WITH SIMULTANEOUS INTRAVENOUS INJECTION OF AN ANTIGEN

| Sulfur Compounds | Doses | | | | | |
|---|---|---|---|---|---|---|
| | 0.625 | 1.25 | 2.5 | 5 | 12.5 | 25 |
| Sodium diethyldithiocarbamate | 0.9 | | 2.5 | 2.5 | 2 | 3.5 |
| Sodium thiomalate | | 2.6 | 3.1 | 3.9 | | |
| Cystine | | 0.98 | | | | |
| Cysteine | | 0.98 | | | | |
| Methionine | | 1.1 | | | | |
| Thiamine | 0.98 | 0.98 | 0.98 | 1.2 | | |
| Sodium thiosulfate | | | 3.5 | | | |
| Sodium metabisulfite | 3.4 | 2.5 | 2.9 | | | |
| Thiophene | | 3.2 | 1.1 | 0.55 | | |

TABLE 1-continued

STIMULATION INDEX BY SUBCUTANEOUS INJECTION OF THE MEDICINE OF THE PRESENT INVENTION WITH SIMULTANEOUS INTRAVENOUS INJECTION OF AN ANTIGEN

| Sulfur Compounds | Doses | | | | | |
|---|---|---|---|---|---|---|
| | 0.625 | 1.25 | 2.5 | 5 | 12.5 | 25 |
| Methimazole | 5.6 | 7.3 | 2.6 | | | |
| Thioguanine | 0.9 | 1.7 | 5.1 | | | |
| Thiouracile | 1.8 | 2.6 | 1.1 | | | |
| Phenothiazine | | 3.5 | 0.3 | | | |
| Thiosemicarbazide | 1.67 | 1.65 | 4.2 | 1.9 | | |

It can be seen in Table I that for 1 dose of 0.625 mg/kg an immunostimulant action is already present for sodium metabisulfite, methimazole, thiouracil and thiosemicabazide. For 1 dose of 1 mg/kg an immunostimulant action is obtained for almost the totality of the sulfur compounds.

Starting with doses of 2.5 mg/kg, certain of the sulfur compounds become less active. However, sodium diethyldithiocarbamate, sodium thiomalate and sodium thiosulfate are active at doses as high as, for instance, 25 mg/kg for sodium diethyldithiocarbamate which is besides not toxic at this dosage.

As a comparison, the index of stimulation of sulfur compounds present in the organism of human beings such as cystine, cysteine, methionine and thiamine has also been studied. At the various dosages contemplated, these compounds are not active.

EXAMPLE 2

In this example the mice were treated in a fashion analogous to those in Example 1, the only difference being that the mice were inoculated with sodium diethyldithiocarbamate 18 hours before the antigen inoculation. The results were as follows:

TABLE 2

INDEX OF STIMULATION

THE PRODUCT OF THE INVENTION BEING INJECTED 18 HOURS BEFORE THE ANTIGEN

| Product | Doses (mg/kg) | | | | |
|---|---|---|---|---|---|
| | 0.625 | 2.50 | 5.0 | 14.5 | 25 |
| Sodium diethyl-dithiocarbamate | 4.4 | 2.45 | 1.2 | 3.8 | 4.7 |

EXAMPLE 3

The same tests as in Example 1 have been effected on mice with the exception that the sulfur compound was injected 6 hours after the antigen inoculation (Table 3) and in a second series of tests, 24 hours after the antigen inoculation (Table 4).

All dosages employed are effective for sodium thiomalate as well as for sodium diethyldithiocarbamate.

TABLE 3

INDEX OF STIMULATION BY SUBCUTANEOUS INJECTION OF THE PRODUCT OF THE INVENTION 6 HOURS AFTER THE ANTIGEN

| Product | Doses (mg/kg) | | | | | |
|---|---|---|---|---|---|---|
| | 0.625 | 1.25 | 2.5 | 5 | 12.5 | 25 |
| Sodium thiomalate | 5.8 | | 4.2 | 3.8 | 12.5 | 2.7 |
| Sodium thiomalate | 5.8 | | 4.2 | 3.8 | 3.0 | 2.7 |
| Sodium diethyl-dithiocarbamate | 0.45 | | 2.10 | 3.8 | 6.2 | 3.1 |
| Sodium thiosulfate | | | 3.5 | | | |
| Sodium metabisulfite | | | 2.0 | | | |

TABLE 3-continued

INDEX OF STIMULATION BY SUBCUTANEOUS INJECTION OF THE PRODUCT OF THE INVENTION 6 HOURS AFTER THE ANTIGEN

| Product | Doses (mg/kg) | | | | | |
|---|---|---|---|---|---|---|
| | 0.625 | 1.25 | 2.5 | 5 | 12.5 | 25 |
| Cystine | | 1 | | | | |
| Cysteine | | 1 | | | | |
| Thiamine | | 1.2 | | | | |

TABLE 4

INDEX OF STIMULATION BY SUBCUTANEOUS INJECTION OF THE PRODUCT OF THE INVENTION 24 HOURS AFTER THE ANTIGEN

| Product | Doses (mg/kg) | | | | | |
|---|---|---|---|---|---|---|
| | 0.625 | 1.25 | 2.5 | 5 | 12.5 | 25 |
| Sodium diethyl-dithiocarbamate | 3.2 | | 1.4 | 1.6 | 3.1 | 4.0 |

EXAMPLE 4

In this example there has been studied the action of sodium diethyldithiocarbamate on the immunologic response of aged mice. CD-1 female mice (more than 9 months old and weighing from 49–54 grams) were inoculated through the veins with $10^8$ red sheep blood corpuscles. The treated mice then received sodium diethyldithiocarbamate 6 hours after the antigen, certain ones 2.5 mg/kg, the remainder 12.5 mg/kg, of this sulfur compound.

Two days after the antigen injection (sheep red blood corpuscles) the mice were sacrificed and their spleens examined. The results are shown in Table 5.

TABLE 5

| Action on aged CD-1 female mice more than 9 months old, 49–54 g (10 mice per lot) | |
|---|---|
| Treatment | $PFC/10^8$ ± SE |
| None | 39 ± 21 |
| $10^8$ sheep red blood corpuscles | 98 ± 37 |
| $10^8$ sheep red blood corpuscles and 2.5 mg/kg DEDTC | 284 ± 79 |
| $10^8$ sheep red blood corpuscles and 12.5 mg/kg DEDTC | 316 ± 58 |

The results show that the administration of sodium diethyldithiocarbamate to very old mice is capable of increasing, according to the treatment doage, from 2.9–3.2 times more than their immunitary potential which has practically been destroyed by immunisenescence. The inoculation of the aged mice raises their immunitary response to a level (316 plate cultures) which is near that of young adult mice, who, injected with the same quantity of antigen, give 380 plate cultures.

EXAMPLE 5

In this test the influence of theophylline on the immunity stimulation by one of the sulfur compounds of the medicines of the invention, i.e. sodium diethyldithiocarbamate, is studied.

In effect, theophylline inhibits the phosphodierestases and stabilizes cyclic 3',5'-adenosine monophosphate (CAMP) by preventing its conversion.

To this effect one has counted the plate cultures of gelled localized hematolysis present in the spleen of mice treated or not with sodium diethyldithiocarbamate, combined or not with theophylline after intravenous injection of $10^8$ sheep red blood corpuscles.

The counting of the plate cultures of hemotolysis has been carried out in accordance with the previously described method.

TABLE 6

Action of theophylline on the stimulation by DEDTC of CD-1 female mice, 20g ±

| Treatment | PFC/$10^8$ ± SE |
|---|---|
| None | 28 ± 5 |
| $10^8$ sheep red blood corpuscles | 852 ± 104 |
| $10^8$ sheep red blood corpuscles and theophylline | 916 ± 101 |
| $10^8$ sheep red blood corpuscles and 0.625 mg/kg DEDTC | 813 ± 48 |
| $10^8$ sheep red blood corpuscles and 2.5 mg/kg DEDTC | 1965 ± 96 |
| $10^8$ sheep red blood corpuscles and 0.625 mg/kg DEDTC and theophylline | 2003 ± 91 |
| $10^8$ sheep red blood corpuscles and 2.5 mg/kg DEDTC and theophylline | 1906 ± 103 |

It can be seen from this table that the theophylline alone, at the dosage employed, does not modify sensibly the number of plate cultures of the mice spleen.

The treatment of mice with 0.625 mg/kg of sodium diethyldithiocarbamate and with 200 mg per mouse of theophylline increases the stimulating power of the medicine. It can be concluded that this sulfur compound acts by the intermediate of the ring of the CAMP which can serve to mediate these stimulating actions.

EXAMPLE 6

In this test the action on mice is studied with a medicine according to the invention based on sodium diethyldithiocarbamate during a toxic attack on the mice. CD-1 female mice weighing 20 ± 1 g received an inoculation of 2.5 mg of brucellic toxin corresponding to the "phenol" fraction of brucella melitensis. It is known that such an inoculation leads to clear toxic emaciation of mice (see Renoux and Renoux, Jr. inf. Diseases, 1973, 127, 139). A first lot of inoculated mice is maintained as a control for the activity of the toxin. A second lot is treated with 2.5 mg/kg of sodium diethyldithiocarbamate, 12 hours after the inoculation of the toxin. Another lot is treated with 5 injections of the same quantity (2.5 mg/kg of sodium diethyldithiocarbamate at day +2, +3, +4, +6 and +7 after the inoculation of the toxin. Lot No. 1 consists of the control mice who did not receive an inoculation. Another lot 5 is a control for the action of sodium diethyldithiocarbamate on mice without a toxin inoculation, each mouse receiving 5 injections under the same conditions, at the same days and hours as the mice of lot 4. These mice are maintained in an air conditioned environment at 24° C. and fed with special foods without antibodies.

The result is shown in FIG. 1 which illustrates at the abscissa, the time in days and at the ordinate, the evolution in weight starting with normal weight.

The mice treated with the sulfur compound 12 hours after the injection of the endotoxin did not lose weight and as early as the 20th day have a weight curve very clearly higher than that of the control. The treated mice at the days +2, +3, +4, +6 and +7 after the injection of the toxin do not lose weight and have as early as the 20th day a weight curve very greatly higher than that of the control.

It can thus be seen that sodium diethyldithiocarbamate possesses an anti-toxic activity combined with an anabolising effect on the mice.

The administration to subjects of the medicines of the invention can, for example, be effected orally or in the form of a solution of the sulfur compound in the indicated dosages, or in the form of a solid with a classic type excipient. As a variant, the administration can be effected by subcutaneous injection, the sulfur compound being preferably dissolved in physiologic water.

In a preferred fashion, the administration of the medicine with the view of producing an increase in immunity is effected by administering at least one dose per day and this, preferably, for a period of several days or several weeks.

In the embodiment where the medicine of the invention includes antigens, the administration of the medicine is effected under the same condition as those of the antigens alone.

What is claimed is:

1. A process for stimulating the immunity of a living organism comprising orally or subcutaneously administering to said organism in an amount effective to stimulate immunity an immunostimulant medicine consisting essentially of sodium diethyldithiocarbamate and an excipient therefor, said sodium diethyldithiocarbamate being administered at a dosage, relative to the weight of the receptor organism, which corresponds to a dosage which produces, in mice having received an injection of sheep red blood corpuscles, a stimulation index equal to or greater than 1.6.

2. The process of claim 1 wherein said dosage administered comprises between 10 and 25 mg/kg of the receptor organism.

3. A process for stimulating the immunity of a living organism comprising orally or subcutaneously administering to said organism in an amount effective to stimulate immunity an immunostimulant medicine consisting essentially of sodium thiomalate and an excipient therefor, said sodium thiomalate being administered at a dosage, relative to the weight of the receptor organism, which corresponds to a dosage which produces, in mice having received an injection of sheep red blood corpuscles, a stimulation index equal to or greater than 1.6.

4. The process of claim 3 wherein said dosage administered comprises between 0.6 and 10 mg/kg of the receptor organism.

5. A process for stimulating the immunity of a living organism comprising orally or subcutaneously administering to said organism in an amount effective to stimulate immunity an immunostimulant medicine consisting essentially of sodium thiosulfate and an excipient therefor, said sodium thiosulfate being administered at a dosage, relative to the weight of the receptor organism, which corresponds to a dosage which produces, in mice having received an injection of sheep red blood corpuscles, a stimulation index equal to or greater than 1.6.

6. The process of claim 5 wherein said dosage administered comprises at least about 1 mg/kg of the receptor organism.

7. A process for stimulating the immunity of a living organism comprising orally or subcutaneously administering to said organism in an amount effective to stimulate immunity an immunostimulant medicine consisting essentially of sodium metabisulfite and an excipient therefor, said sodium metabisulfite being administered at a dosage, relative to the weight of the receptor organism, which corresponds to a dosage which produces, in mice having received an injection of sheep red blood corpuscles, a stimulation index equal to or greater than 1.6.

8. A process for stimulating the immunity of a living organism comprising orally or subcutaneously administering to said organism in an amount effective to stimulate immunity an immunostimulant medicine consisting essentially of thiosemicarbazide and an excipient therefor, said thiosemicarbazide being administered at a dosage, relative to the weight of the receptor organism, which corresponds to a dosage which produces, in mice having received an injection of sheep red blood corpuscles, a stimulation index equal to or greater than 1.6.

* * * * *